United States Patent [19]

Ashworth et al.

[11] 4,256,655

[45] Mar. 17, 1981

[54] METHOD FOR MAKING THIOBISCARBAMATES

[75] Inventors: Robert W. Ashworth, Hackettstown, N.J.; Wallace Y. Fu, South Charleston, W. Va.

[73] Assignee: Union Carbide Corporation, New York, N.Y.

[21] Appl. No.: 70,535

[22] Filed: Sep. 5, 1979

[51] Int. Cl.$^3$ ............................................. C07C 119/00
[52] U.S. Cl. ............................................. 260/453 RW
[58] Field of Search ................................. 260/453 RW

[56] References Cited

U.S. PATENT DOCUMENTS 4,004,031   1/1977   Drabek ............................. 424/300

*Primary Examiner*—Henry R. Jiles
*Assistant Examiner*—Robert C. Whittenbaugh
*Attorney, Agent, or Firm*—Dale Lynn Carlson

[57] ABSTRACT

Method of preparing thiobiscarbamates by reacting nitrogen-containing heterocyclic base and sulfur monochloride or sulfur dichloride and reacting the resulting base-sulfur chloride adduct with carbamate to form thiobiscarbamates.

13 Claims, No Drawings

METHOD FOR MAKING THIOBISCARBAMATES

BACKGROUND

This invention relates to the manufacture of thiobiscarbamates having the formula $$\left( \begin{array}{c} CH_3-C=N-O-C-N \\ | \quad \quad \quad \| \; | \\ S-R_1 \quad \quad O \; CH_3 \end{array} \right)_2 S \quad (I)$$

wherein $R_1$, is methyl, ethyl, n-propyl, isopropyl, n-butyl or isobutyl and $$\left( \begin{array}{c} O \\ \| \\ R_2-C=N-O-C-N \\ | \quad \quad \quad \quad | \\ R_3 \quad \quad \quad \quad CH_3 \end{array} \right)_2 S \quad (II)$$

wherein $R_2$ is methyl, ethyl, n-propyl, isopropyl, n-butyl, isobutyl, or $CH_3S(CH_3)_2C-$ and $R_3$ is H or $CH_2X$ where X is $-SCH_3$, $$-\overset{O}{\underset{\|}{S}}-CH_3, \text{ or } -\overset{O}{\underset{\underset{O}{\|}}{\overset{\|}{S}}}-CH_3.$$

These biscarbamate compounds are known to have pesticidal activity.

U.S. Pat. No. 4,004,031 discloses a method of making these compounds involving simultaneous reaction of carbamate, base, and sulfur chloride ($SCl_2$ or $S_2Cl_2$). A disadvantage of this prior art method is its relatively low yield of products and high production of undesirable bi-products.

OBJECTS

It is an object of this invention to provide a method for making thiobiscarbamate compounds that produces higher yields.

It is another object of this invention to provide a method for making thiobiscarbamate compounds that produces less biproduct.

SUMMARY OF THE INVENTION

These and other objects are attained by the present invention one aspect of which comprises:

A method for making a compound of the formula $$\left( \begin{array}{c} CH_3-C=N-O-C-N \\ | \quad \quad \quad \| \; | \\ S-R_1 \quad \quad O \; CH_3 \end{array} \right)_2 S$$

wherein R, is methyl, ethyl, n-propyl, isopropyl, n-butyl or isobutyl comprising the steps of:

(a) in presence of solvent, reacting nitrogen-containing heterocyclie base with a sulfur chloride selected from the groups of $SCl_2$, $S_2Cl_2$, and mixtures thereof to form base-sulfur chloride adduct, and thereafter (b) in presence of solvent, reacting said adduct with carbamate of the formula $$CH_3-C=N-O-C-N-H \\ | \quad \quad \quad \| \; | \\ S-R_1 \quad \quad O \; CH_3$$

wherein R, is as previously defined.

A second aspect of the invention comprises:

A method for making a compound of the formula $$\left( \begin{array}{c} O \\ \| \\ R_2-C=N-O-C-N \\ | \quad \quad \quad \quad | \\ R_3 \quad \quad \quad \quad CH_3 \end{array} \right)_2 S$$

wherein $R_2$ is methyl, ethyl, n-propyl, isopropyl, n-butyl, or $CH_3S(CH_3)_2C-$ and $R_3$ is H or $-CH_2X$ wherein X is $-SCH_3$, $$-\overset{O}{\underset{\|}{S}}-CH_3 \text{ or } -\overset{O}{\underset{\underset{O}{\|}}{\overset{\|}{S}}}-CH_3$$

comprising the steps of (a) in presence of solvent, reacting nitrogen-containing heterocyclic base with a sulfur chloride selected from the groups of $SCl_2$, $S_2Cl_2$, and mixtures thereof to form base-sulfur chloride adduct, and (b) in presence of solvent, reacting said adduct with carbamate of the formula $$R_2-C=N-O-\overset{O}{\underset{\|}{C}}-N-H \\ | \quad \quad \quad \quad \quad | \\ R_3 \quad \quad \quad \quad CH_3$$

wherein $R_2$ and $R_3$ are as previously defined.

This invention is predicated on the discovery that complexing nitrogen-containing heterocyclic base with sulfur chloride in presence of a solvent to form an adduct and thereafter reacting carbamate with the adduct provides a surprising increase in yield. This change in the order of addition of the reactants over that of the prior art is especially effective if the solvent is xylene, and if the sulfur chloride used is $SCl_2$.

DETAILED DESCRIPTION OF THE INVENTION

The first step in making thiobiscarbamate compound in accordance with the present invention is to react nitrogen-containing heterocyclic base and sulfur chloride in presence of solvent to form base-sulfur chloride adduct, believed to occur in accordance with the following equation:

$$2\,B + SCl_2 \longrightarrow \underset{\underset{\text{adduct}}{Cl^- \quad Cl^-}}{B-S-B} \\ \text{base sulfur} \\ \text{dichloride}$$

$$2\,B + S_2Cl_2 \longrightarrow \underset{\underset{\text{adduct}}{Cl^- \quad Cl^-}}{B-S-S-B} \\ \text{base sulfur mono} \\ \text{chloride}$$

Hence, as used throughout the present specification and claims, the term "nitrogen-containing heterocyclic base" is intended to mean a compound of that type that is capable of reacting with sulfur chloride in presence of solvent to form an adduct of nitrogen-containing heterocyclic base and sulfur chloride.

Preferably sufficient base is used so that all of the sulfur chloride is reacted. The preferred bases are pyridine and 2-ethyl-5-methyl pyridine.

Preferred solvent are aromatic hydrocarbons.

The most preferred solvent is commercial grade xylene, i.e. mixed xylenes of commercial purity. However, many solvents are acceptable, including but not limited to halogenated hydrocarbons such as dichloromethane, chloroform, carbon tetrachloride, tetrachloroethane; ethers such as diethyl ether, tetrahydrofuran, 1,4-dioxane, diisopropyl ether, diphenyl ether, anisole; aromatic solvents such as benzene, toluene, o-xylene, m-xylene, p-xylene, ethylbenzene, mesitylene, t-butylbenzene, chlorobenzene, nitrobenzene; and other organic solvents such as N,N-dimethylacetamide, N,N-dimethylformamide, acetonitrile, hexane, cyclohexane and methylcyclohexane.

Sulfur dichloride is the preferred sulfur chloride. However, this compound decomposes slowly according to the equation $$2SCl_2 \rightleftharpoons S_2Cl_2 + Cl_2.$$

Hence commercial $SCl_2$, which currently is believed to contain roughly 70 to 85% $SCl_2$, is a practical and acceptable sulfur chloride. Sulfur monochloride, $S_2Cl_2$, is also acceptable, as are mixtures of $SCl_2$ and $S_2Cl_2$.

The reaction between base and sulfur chloride is preferably carried out for about 0.25 to 1 hour at temperatures between about $-10°$ and $50°$ C. More preferably the reaction temperature is about $-10°$ C. to $30°$ C. and the reaction time about 20 min to 60 min.

The second step in the process is to react the adduct with carbamate in the presence of solvent. A preferred carbamate is methomyl. With pyridine as the base, the reaction between methomyl and base-sulfur dichloride adduct is believed to proceed as follows:

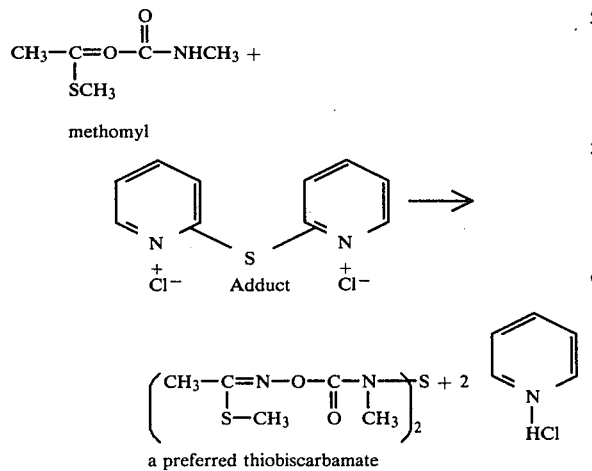

a preferred thiobiscarbamate

The solvents acceptable for the first step in the process, the adduct forming step, are also acceptable for the second step, the reaction with carbamate. The preferred solvent for the second step is again xylene, but other solvents are acceptable. Since the first step yields an adduct-solvent mixture, preferably the second step is preformed by adding carbamate to the adduct-solvent mixture resulting from the first step. Of course, the adduct could be separated from the solvent used for the first step and a different solvent used for the second step, but such extra processing is not necessary.

The second step is preferably carried out at a temperature of from about $20°$ C. to $45°$ C., more preferably about $20°$ C. to $32°$ C., and for a reaction time of about 1 hour to 96 hours, more preferably about 1 hour to 20 hours.

EXAMPLES

Examples 1 to 12 illustrate practice of the invention and examples 13 to 28 illustrate the prior art method. All experiments were conducted under nitrogen atmosphere in a 500 ml, four-necked flask equipped with a thermometer, a mechanical stirrer, a drying tube, and a pressure equalizing addition funnel attached to a nitrogen inlet tube. The assembled apparatus was dried with a heat gun under a nitrogen atmosphere prior to the experiments.

PROCEDURE FOR EXAMPLES 1 to 10

The first step was preformed as follows:

The adduct was formed by preparing a solution of 28.5 g. pyridine and 200 g. solvent at about $2°$ C. Sulfur chloride in the amount of 20.74 grams was added to the solution dropwise over a 15 minute period while maintaining temperature of $2°-4°$ C. The adduct precipitated. The adduct-solvent mixture was stirred for 30 minutes.

The second step in the process was preformed as follows:

Methomyl in the amount of 53.53 g was added to the mixtures and the temperature was allowed to rise to the reaction temperature. This temperature was maintained for the reaction time while stirring.

The reaction mixture was filtered and the cake washed twice with a 150 g of fresh solvent. The filtered cake was then washed four times with 150 g of water at $40°$ C. The cake was dried and analyzed for purity of the thiobiscarbamate compound. The yield was calculated multiplying the weight of the dried filter cake by the purity in weight % and dividing by the theoritical yield of the biscarbamate compound. The results appear in Table I.

PROCEDURE FOR EXAMPLES 11 AND 12

These experiments were preformed the same as example 1 to 10 except as noted in foot notes c and d in Table I.

TABLE I

EXAMPLES USING THE PRESENT INVENTION

| EXAMPLE | SOLVENT | SULFUR[a] CHLORIDE | 2ND STEP REACTION TIME(HR) | 2ND STEP REACTION TEMP(°C.) | DRIED CAKE WT. (g) | PURITY | % ABS* YIELD |
|---------|---------|-------------------|----------------------------|------------------------------|---------------------|--------|--------------|
| 1  | Toluene          | $SCl_2$   | 4  | 30 | 32.76 | 97.5 | 64.9 |
| 2  | Toluene          | $SCl_2$   | 5  | 30 | 37.04 | 96.5 | 62.8 |
| 3  | Toluene          | $SCl_2$   | 16 | 35 | 37.24 | 98.7 | 62.8 |
| 4  | Xylene[b]        | $SCl_2$   | 5  | 25 | 34.08 | 98.4 | 76.6 |
| 5  | Xylene[b]        | $SCl_2$   | 11 | 25 | 37.87 | 94.0 | 81.3 |
| 6  | Xylene[b]        | $SCl_2$   | 20 | 25 | 55.46 | 96.3 | 91.3 |
| 7  | $CH_2Cl_2$       | $SCl_2$   | 2  | 25 | 30.61 | 93.6 | 49.0 |
| 8  | $CH_2Cl_2$       | $SCl_2$   | 4  | 25 | 31.27 | 94.7 | 50.7 |
| 9  | Ethylbenzene     | $SCl_2$   | 20 | 25 | 30.87 | 95.3 | 50.3 |
| 10 | Ethyl ether      | $SCl_2$   | 20 | 25 | 46.63 | 89.5 | 71.4 |
| 11[c] | Toluene       | $S_2Cl_2$ | 16 | 40 | 44.60 | 98.2 | 74.9 |
| 12[d] | Xylene        | $SCl_2$   | 66 | 25 | 48.96 | 90.2 | 75.5 |

[a]Commercial grade $SCl_2$ believed to be about ≦85% $SCl_2$ by wt.
[b]Commercial grade mixed xylene containing about 19% o, 42% m, 18% p xylene and 21% ethylbenzene.
[c]Sulfur monochloride (23.13 g) was added to a solution of 27.10 g of pyridine in 250 ml of toluene at 25°–30° C. After 15 minutes, 53.53 g of methomyl was added at once and then heated to 40° C. for 16 hours. After filtration, toluene washing and water washing, the product was vacuum dried to give 44.60 g of product.
[d]2-Ethyl-5-methylpyridine (46.3 g) was substituted for pyridine.

PROCEDURE FOR EXAMPLES 13 TO 28

A suspension of 50 g methomyl, 25 g base, and 300 ml solvent was prepared and warmed to the reaction temperature. To the suspension was added 16.5 g sulfur chloride dissolved in 20 ml solvent. The reaction temperature was maintained for the reaction time listed in the table. The resulting slurry was filtered and the cake washed with 300 ml of cold water twice, and then triturated twice with 300 ml of methanol and filtered. The solid was vacuum dried at 45° C. for 2 hours. The results are listed in Table II. The yield was calculated the same way it was for Examples 1 to 12.

Variations to the above procedure for certain examples are described in the foot note to Table II.

TABLE II

EXAMPLE USING PRIOR ART METHOD

| EXAMPLE | SOLVENT | SULFUR CHLORIDE | BASE | REACTION TIME(HR) | REACTION TEMP(°C.) | WT. OF PRODUCT (g) | PURITY (BY LC) | % ABS* YIELD |
|---------|---------|-----------------|------|-------------------|--------------------|--------------------|----------------|--------------|
| 13    | $CH_2Cl_2$  | $SCl_2$   | pyridine             | 16   | −10 to 25 | 22.40 | 90.9  | 37.1 |
| 14    | Toluene     | $SCl_2$   | pyridine             | 48   | 20 to 28  | 40.99 | 97.4  | 70.4 |
| 15[a] | $CH_3CN$    | $SCl_2$   | pyridine             | 16   | 25 to 35  | 2.96  | 94.9  | 4.9  |
| 16    | Hexane      | $SCl_2$   | pyridine             | 16   | 25 to 40  | 27.08 | 91.5  | 43.7 |
| 17    | p-Xylene    | $SCl_2$   | pyridine             | 16   | 20 to 30  | 41.55 | 96.4  | 70.7 |
| 18    | Pyridine    | $SCl_2$   | pyridine             | 19   | 20 to 30  | 41.27 | 93.5  | 68.1 |
| 19[a] | DMF         | $SCl_2$   | pyridine             | 20   | 0 to 10   | 37.25 | 92.1  | 60.5 |
| 20    | o-Xylene    | $SCl_2$   | pyridine             | 18.5 | 20 to 30  | 39.09 | 89.1  | 60.9 |
| 21    | Ethylbenzene| $SCl_2$   | pyridine             | 4    | 30        | 29.34 | 94.1  | 47.0 |
| 22    | Xylenes     | $SCl_2$   | pyridine             | 4    | 30        | 38.03 | 87.5  | 56.9 |
| 23    | Toluene     | $SCl_2$   | TEA[c]               | 19   | 23        | 13.88 | 82.3  | 15.3 |
| 24    | p-Xylene    | $SCl_2$   | quinoline[d]         | 2    | 25        | 32.64 | 64.3  | 37.0 |
| 25    | Cyclohexane | $SCl_2$   | methylethyl-pyridine[e] | 1 | 30        | 27.24 | 85.4  | 41.0 |
| 26    | Toluene     | $SCl_2$   | isoquinoline[f]      | 16   | 35        | 38.07 | 85.36 | 57.29 |
| 27    | $CH_2Cl_2$  | $S_2Cl_2$ | pyridine             | 18   | 35        | 33.58 | 89.0  | 64.5 |
| 28[b] | THF/Benzene | $S_2Cl_2$ | pyridine             | 10   | 0         | 7.00  | 95.2  | 18.9 |

[a]$SCl_2$ was added without solvent dilution.
[b]Done exactly as described in U.S. Pat. No. 4,004,031 (Ciba-Geigy) issued January 18, 1977.
[c]Triethylamine (36 g) was substituted for the pyridine.
[d]Quinoline (40.81 g) was substituted for the pyridine.
[e]Methylethylpyridine (40.81 g) was substituted for the pyridine.
[f]Isoquinoline (40.81 g) was substituted for the pyridine.

The superiority of the present invention can readily be seen by comparing examples 4, 5 and 6 wherein yields of 76.6, 81.3 and 91.3% were attained, with prior art examples 17, 20 and 22 wherein yields of only 70.7, 60.9 and 56.9 were attained using the same or similar solvent and the same base. Further evidence of the present methods superiority can be ascertained by comparing examples 7 and 8 (49.0 and 50.7% yields) with prior art example 13 wherein only 37.1% yield was attained using $CH_2Cl_2$ as the solvent, and pyridine as the base in both methods.

Example 11 shows that good yields (here 74.9%) can be attained by the present invention using $S_2Cl_2$. Likewise, example 12 shows that the present invention can achieve a good yield with 2-ethyl-5-methyl pyridine as the base.

What is claimed is:

1. A method for making a compound of the formula

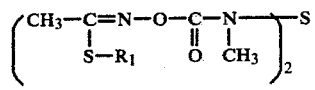

wherein $R_1$ is methyl, ethyl, n-propyl, isopropyl, n-butyl or isobutyl comprising the steps of:
   (a) In presence of solvent, reacting nitrogen-containing hetrocyclic base with a sulfur chloride selected from the groups of $SCl_2$, $S_2Cl_2$, and mixtures thereof to form base-sulfur chloride adduct, and (b) In presence of solvent, reacting said adduct with carbamate of the formula

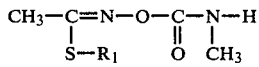

wherein $R_1$ is a previously defined.

2. A method for making a compound of the formula

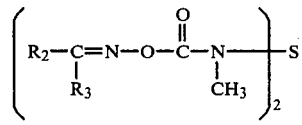

wherein $R_2$ is methyl, ethyl, n-propyl, isopropyl, n-butyl, or $CH_3S(CH_3)_2C$— and $R_3$ is H or —$CH_2X$ wherein X is —$SCH_3$,

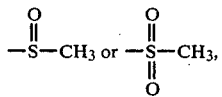

comprising the steps of (a) in presence of solvent, reacting nitrogen-containing heterocyclic base with a sulfur chloride selected from the groups of $SCl_2$, $S_2Cl_2$, and mixtures thereof to form base-sulfur chloride adduct, and (b) in presence of solvent, reacting said adduct with carbamate of the formula

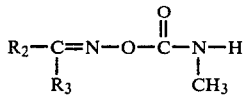

wherein $R_2$ and $R_2$ are as previously defined.

3. The process of claim 1 wherein $R_1$ is methyl.

4. The process of claim 3 wherein said base is pyridine.

5. The process of claim 4 wherein said sulfur chloride is $SCl_2$.

6. The process of claim 4 wherein said sulfur chloride is commercial grade $SCl_2$.

7. The process of claim 4 wherein said step (a) solvent and said step (b) solvent is xylene.

8. The process of claim 4 or 7 wherein said sulfur chloride is $S_2Cl_2$.

9. The process of claims 4, 5, and 6 wherein said step (a) solvent and said step (b) solvent is $CH_2Cl_2$.

10. The process of claim 5 wherein said step (a) and step (b) solvent is xylene.

11. The process of claim 6 wherein said step (a) and step (b) solvent is xylene.

12. The process of claims 4, 5, 6, 7, 10, or 11 wherein step (a) is carried out at temperature of from about $-10°$ C. to $50°$ C. for about 0.25 to 1 hour, and step (b) is carried out at temperature of from about $20°$ C. to $45°$ C. for about 1 to 96 hours.

13. The process of claim 12 wherein step (a) is carried out at temperature of from about $-10°$ C. to $30°$ C. for about 20 minutes to 60 minutes, and step (b) is carried out at temperature of from about $20°$ C. to $32°$ C. for about 1 to 20 hours.

* * * * *